(12) United States Patent
Schmid

(10) Patent No.: US 10,737,024 B2
(45) Date of Patent: Aug. 11, 2020

(54) FLUID DELIVERY AND INFUSION DEVICES, AND METHODS OF USE THEREOF

(71) Applicant: Insulet Corporation, Billerica, MA (US)

(72) Inventor: Kevin G. Schmid, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 300 days.

(21) Appl. No.: 15/047,028

(22) Filed: Feb. 18, 2016

(65) Prior Publication Data

US 2016/0235908 A1 Aug. 18, 2016

Related U.S. Application Data

(60) Provisional application No. 62/117,937, filed on Feb. 18, 2015.

(51) Int. Cl.
| | |
|---|---|
| *A61M 5/14* | (2006.01) |
| *A61M 5/172* | (2006.01) |
| *A61M 5/142* | (2006.01) |
| *A61M 5/158* | (2006.01) |

(52) U.S. Cl.
CPC ...... *A61M 5/1723* (2013.01); *A61M 5/14248* (2013.01); *A61M 2005/1402* (2013.01); *A61M 2005/14208* (2013.01); *A61M 2005/14252* (2013.01); *A61M 2005/1585* (2013.01); *A61M 2005/1726* (2013.01)

(58) Field of Classification Search
CPC .. A61M 5/142; A61M 5/14248; A61M 5/172; A61M 5/14244; A61M 5/168; A61M 5/1684; A61M 5/1723; A61M 5/20; A61M 5/204; A61M 5/3287; A61M 2005/1402; A61M 2005/14208; A61M 2005/14252; A61M 2005/1585; A61M 2205/52

See application file for complete search history.

(56) References Cited

U.S. PATENT DOCUMENTS

| | | | |
|---|---|---|---|
| 3,963,380 | A | 6/1976 | Thomas, Jr. et al. |
| 5,153,827 | A | 10/1992 | Coutre et al. |
| 5,421,812 | A | 6/1995 | Langley et al. |
| 7,018,360 | B2 | 3/2006 | Flaherty et al. |

(Continued)

OTHER PUBLICATIONS

PCT International Search Report and Written Opinion dated Apr. 29, 2015, received in corresponding PCT Application No. PCT/US16/18452, 9 pgs.

(Continued)

*Primary Examiner* — Kevin C Sirmons
*Assistant Examiner* — Tezita Z Watts

(57) ABSTRACT

A medical device comprising an infusion device comprising a fluid reservoir to contain a therapeutic fluid and a transcutaneous access tool fluidly coupled to the fluid reservoir, the transcutaneous access tool configured to deliver the therapeutic fluid subcutaneously to a patient; wherein the infusion device operates in a stand-by mode prior to the therapeutic fluid being introduced into the fluid reservoir; wherein the infusion device operates to deploy the transcutaneous access tool within a predetermined deployment time period upon filling the fluid reservoir to a predetermined fill level with the therapeutic fluid.

16 Claims, 20 Drawing Sheets

(56) References Cited

U.S. PATENT DOCUMENTS

| | | |
|---|---|---|
| 7,128,727 B2 | 10/2006 | Flaherty et al. |
| 7,144,384 B2 | 12/2006 | Gorman |
| 8,547,239 B2 | 10/2013 | Peatfield et al. |
| 9,061,097 B2 | 6/2015 | Holt et al. |
| 2001/0034023 A1 | 10/2001 | Stanton, Jr. et al. |
| 2001/0034502 A1 | 10/2001 | Moberg et al. |
| 2002/0016568 A1 | 2/2002 | Lebel et al. |
| 2003/0135388 A1 | 7/2003 | Martucci et al. |
| 2003/0220605 A1 | 11/2003 | Bowman, Jr. et al. |
| 2004/0010207 A1 | 1/2004 | Flaherty et al. |
| 2005/0075624 A1 | 4/2005 | Miesel |
| 2005/0238507 A1 | 10/2005 | DiIanni et al. |
| 2006/0173406 A1* | 8/2006 | Hayes ................ A61B 5/14532 604/67 |
| 2006/0270983 A1 | 11/2006 | Lord et al. |
| 2006/0282290 A1 | 12/2006 | Flaherty et al. |
| 2007/0118405 A1 | 5/2007 | Campbell et al. |
| 2008/0206067 A1 | 8/2008 | De Corral et al. |
| 2009/0318791 A1 | 12/2009 | Kaastrup |
| 2010/0057042 A1 | 3/2010 | Hayter |
| 2010/0211003 A1 | 8/2010 | Sundar et al. |
| 2011/0160652 A1* | 6/2011 | Yodfat ................ A61M 5/1456 604/66 |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1* | 9/2011 | Remde ............. A61M 5/14248 604/151 |
| 2012/0053556 A1* | 3/2012 | Lee .................. A61M 5/16877 604/500 |
| 2012/0203178 A1 | 8/2012 | Tverskoy |
| 2012/0282111 A1 | 11/2012 | Nip et al. |
| 2012/0295550 A1 | 11/2012 | Wilson et al. |
| 2013/0253472 A1 | 9/2013 | Cabiri |
| 2013/0317753 A1 | 11/2013 | Kamen et al. |
| 2013/0338576 A1 | 12/2013 | Oconnor et al. |
| 2015/0265767 A1* | 9/2015 | Vazquez ............... A61M 5/162 604/500 |
| 2016/0331310 A1 | 11/2016 | Kovatchev |
| 2017/0173261 A1 | 6/2017 | OConnor et al. |
| 2017/0189625 A1 | 7/2017 | Cirillo et al. |
| 2018/0036495 A1 | 2/2018 | Searle et al. |
| 2018/0204636 A1 | 7/2018 | Edwards et al. |

OTHER PUBLICATIONS

Extended Search Report dated Aug. 13, 2018, issued in European Patent Application No. 16753053.4, 9 pages.
International Preliminary Report on Patentability dated Aug. 31, 2017, issued in PCT Patent Application No. PCT/US2016/018452, 7 pages.
International Search Report and Written Opinion for the International Patent Application No. PCT/US2019/055862, dated Mar. 11, 2020, 20 pages.

* cited by examiner

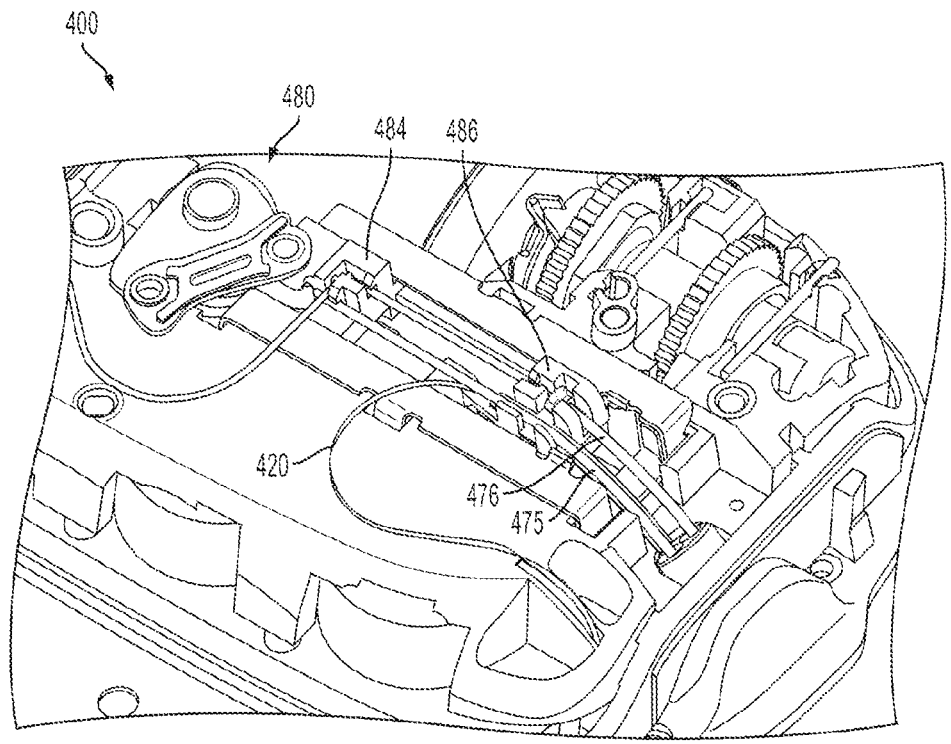
FIG. 39
FIG. 40
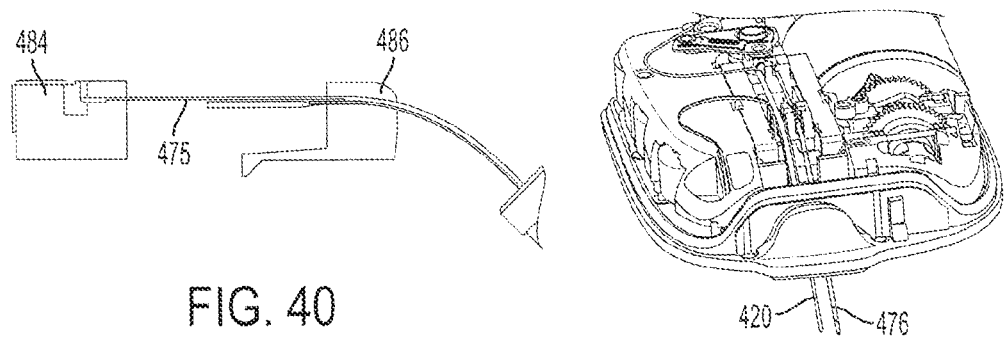
FIG. 41

ND INFUSION
FLUID DELIVERY AND INFUSION DEVICES, AND METHODS OF USE THEREOF

CROSS REFERENCE TO RELATED APPLICATIONS

This application claims the benefit of U.S. provisional application No. 62/117,937 filed Feb. 18, 2015, which is hereby incorporated by reference in its entirety.

TECHNICAL FIELD

The present invention relates to medical devices, such as fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump and/or to improve the comfort to the user. These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously.

In certain embodiments, the fluid delivery device may comprise an ambulatory infusion device to administer a liquid medicine or other therapeutic fluid to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, an infusion device may comprise a fluid reservoir for containing a therapeutic fluid; and a transcutaneous access tool fluidly coupled to the fluid reservoir, which may deliver the therapeutic fluid subcutaneously and introduce a monitoring test strip subcutaneously.

In certain embodiments, a method to treat a patient may be provided comprising providing an infusion device with integrated monitoring, with the device comprising a fluid reservoir for containing a therapeutic fluid; and a transcutaneous access tool fluidly coupled to the fluid reservoir, which may deliver the therapeutic fluid subcutaneously and introduce a monitoring test strip subcutaneously; delivering the therapeutic fluid subcutaneously with the transcutaneous access tool to a patient, and introducing the monitoring test strip subcutaneously with the transcutaneous access tool to the patient.

In certain embodiments, the transcutaneous access tool includes a needle/trocar, and the transcutaneous access tool insertion mechanism is configured to insert and retract the needle/trocar in a single, uninterrupted motion. In such a manner, the pain of insertion and retraction of the needle/trocar experienced by the patient may be reduced.

In certain embodiments, the fluid delivery device may comprise a fluid reservoir; a transcutaneous access tool fluidly coupled to the fluid reservoir, the transcutaneous access tool including a needle/trocar; and a transcutaneous access tool insertion mechanism for deploying the transcutaneous access tool, wherein the insertion mechanism is configured to insert and retract the needle/trocar in a single, uninterrupted motion.

In certain embodiments, the fluid delivery device may comprise a fluid reservoir; a transcutaneous access tool fluidly coupled to the fluid reservoir, the transcutaneous access tool including at least a needle/trocar; and a transcutaneous access tool insertion mechanism for deploying the transcutaneous access tool, wherein the insertion mechanism is configured to insert the needle/trocar with an increasing insertion force as the needle/trocar moves in an insertion direction.

In certain embodiments, the transcutaneous access tool insertion mechanism for deploying a transcutaneous access tool including a cannula and a needle/trocar located inside of the cannula may comprise a first sliding member configured to move the needle/trocar in an insertion direction and a retraction direction; a second sliding member configured to move the cannula in the insertion direction; a torsion spring; and linkages coupled between the torsion spring and the first sliding member such that energy stored in the torsion spring causes the linkages to move the first sliding member in the insertion direction and the retraction direction.

In certain embodiments, the drive mechanism may comprise a clutch mechanism. As explained herein, by using a clutch mechanism, the number of fluid path prime pulses to prime the pump may be reduced and a full and proper priming of the fluid path before placement on the body may be better assured. The clutch mechanism may also be made suitable for other drug applications without significant redesign, and be more easily inspected than conventional drive mechanisms for infusion devices.

In certain embodiments, the fluid delivery device may comprise a fluid reservoir; a transcutaneous access tool fluidly coupled to the fluid reservoir; and a drive mechanism for driving fluid from the reservoir. The drive mechanism may comprise a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through the clutch mechanism when disengaged and is configured to grip the nut when engaged such that the drive wheel rotates the nut to advance the leadscrew and the plunger into the reservoir.

In certain embodiments, the fluid delivery device may comprise a fluid reservoir; a transcutaneous access tool fluidly coupled to the fluid reservoir; and a drive mechanism for driving fluid from the reservoir The drive mechanism may comprise a plunger received in the reservoir; an elongated assembly comprising a first elongated member and a second elongated member; the first elongated member extending from the plunger; the second elongated member coupled to the first elongated member; a drive wheel; and a clutch mechanism coupled to the drive wheel, wherein the clutch mechanism is configured to allow the second elongated member to pass through when disengaged and is configured to grip the second elongated member when engaged such that the drive wheel rotates the second elongated member to advance the first elongated member and the plunger into the reservoir.

In certain embodiments, a method of operating a foregoing fluid delivery device may comprise providing the fluid delivery device; holding the clutch mechanism in a disengaged position; filling the fluid reservoir with fluid; passing the second elongated member through the clutch mechanism such that the plunger is retracted within the reservoir; releasing the clutch mechanism from the disengaged position; and engaging the clutch mechanism with the second elongated member.

In certain embodiments, present disclosure provides a medical device comprising an infusion device comprising a fluid reservoir to contain a therapeutic fluid and a transcutaneous access tool fluidly coupled to the fluid reservoir, the transcutaneous access tool configured to deliver the therapeutic fluid subcutaneously to a patient; wherein the infusion device operates in a stand-by mode prior to the therapeutic fluid being introduced into the fluid reservoir; wherein the infusion device operates to deploy the transcutaneous access tool within a predetermined deployment time period upon filling the fluid reservoir to a predetermined fill level with the therapeutic fluid.

In certain embodiments, the predetermined deployment time period may be greater than or equal to 30 seconds, and/or the predetermined deployment time period may be less than or equal to 15 minutes. In other embodiments, the transcutaneous access tool introduction time period may be greater than or equal to 1 minute, and/or less than or equal to 10 minutes. In other embodiments, the transcutaneous access tool introduction time period may be greater than or equal to 2 minutes, and/or less than or equal to 5 minutes.

In certain embodiments, the infusion device may comprise a non-transitory memory including stored instructions that, when executed by at least one processor, cause the infusion device to deploy the transcutaneous access tool within the predetermined deployment time period.

In certain embodiments, the infusion device may comprise at least one sensor, wherein the at least one sensor may operate by sending an input signal to the at least one processor when the therapeutic fluid in the fluid reservoir reaches the predetermined fill level.

In certain embodiments, the at least one processor may operate by detecting the input signal from the at least one sensor, and upon detecting the input signal from the at least one sensor, the at least one processor may operate to execute the instructions that cause the infusion device to deploy the transcutaneous access tool within the predetermined deployment time period.

In certain embodiments, the infusion device may operate to deliver the therapeutic fluid in the fluid reservoir through the transcutaneous access tool after a predetermined infusion delay time period. The infusion device may operate to initiate the predetermined infusion delay time period when the transcutaneous access tool is deployed. The predetermined infusion delay time period may be at least 1 hour, at least 8 hours, at least 16 hours or at least 20 hours.

In certain embodiments, a method of treating a patient is provided, comprising introducing a therapeutic fluid to an infusion device, wherein the infusion device comprises a fluid reservoir which contains the therapeutic fluid, and a transcutaneous access tool fluidly coupled to the fluid reservoir, the transcutaneous access tool to deliver the therapeutic fluid subcutaneously to the patient; securing the infusion device to the patient; introducing the transcutaneous access tool into the patient; delivering the therapeutic fluid subcutaneously to a patient with the transcutaneous access tool; and wherein the infusion device introduces the transcutaneous access tool into the patient within a transcutaneous access tool introduction time period after introducing a therapeutic fluid to the infusion device, wherein the transcutaneous access tool introduction time period is greater than or equal to 30 seconds, and less than or equal to 15 minutes.

In certain embodiments, the infusion device may comprise a non-transitory memory configured to store instructions that, when executed by at least one processor, cause the infusion device to introduce the transcutaneous access tool into the patient within the transcutaneous access tool introduction time period after the therapeutic fluid is introduced to the infusion device.

In certain embodiments, the infusion device may comprise a sensor which sends an input signal detected by the at least one processor when the fluid contained in the fluid reservoir reaches a predetermined level.

In certain embodiments, the input signal from the sensor may cause the at least one processor to execute the instructions that cause the infusion device to introduce the transcutaneous access tool into the patient within the transcutaneous access tool introduction time period after the therapeutic fluid is introduced to the infusion device.

In certain embodiments, the transcutaneous access tool introduction time period may be greater than or equal to 1 minute, and/or less than or equal to 10 minutes. In certain embodiments, the transcutaneous access tool introduction time period may be greater than or equal to 2 minutes, and/or less than or equal to 5 minutes.

In certain embodiments, the infusion device may deliver the therapeutic fluid subcutaneously to a patient with the transcutaneous access tool after an infusion delay time period which is initiated when the transcutaneous access tool is introduced into the patient, wherein the predetermined time period is at least 1 hour. In certain embodiments, the infusion delay time period may be at least 8 hours, at least 16 hours or at least 20 hours.

BRIEF DESCRIPTION OF THE DRAWINGS

These and other features and advantages will be better understood by reading the following detailed description, taken together with the drawings wherein:

FIGS. 35-41 are views of another embodiment of a fluid delivery device including an oval trocar for inserting a monitor test strip transcutaneously;

DETAILED DESCRIPTION

Figure 1:
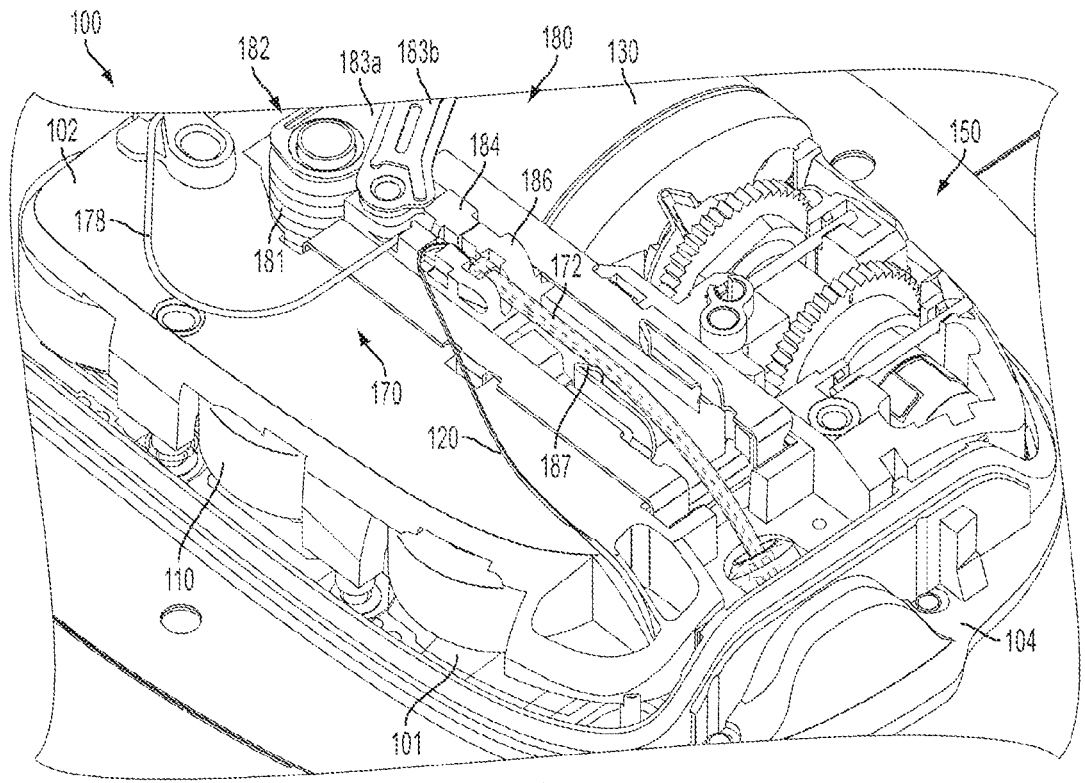
FIG. 1 is a top perspective view of a fluid delivery device with a transcutaneous access tool insertion mechanism in a pre-deployment position, consistent with the present disclosure.
Figure 2:
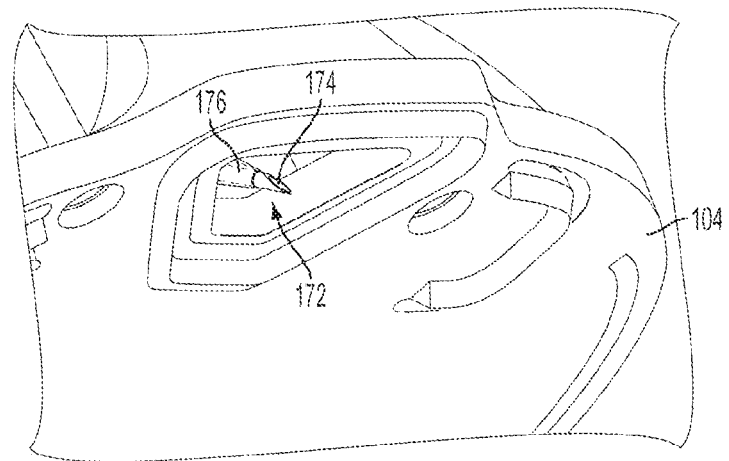
FIG. 2 is a bottom perspective view of a needle and cannula retracted into the fluid delivery device in the pre-deployment position shown in FIG. 1.
Figure 3:
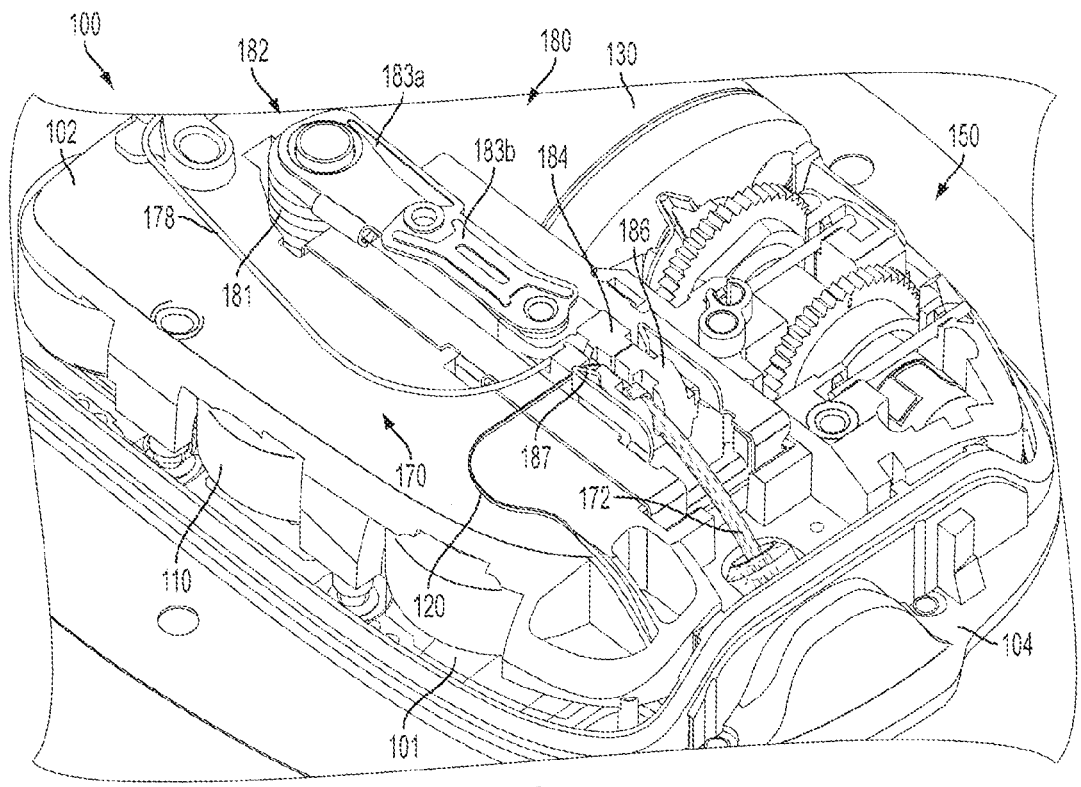
FIG. 3 is a top perspective view of the fluid delivery device shown in FIG. 1 with the insertion mechanism in an intermediate position.
Figure 4:
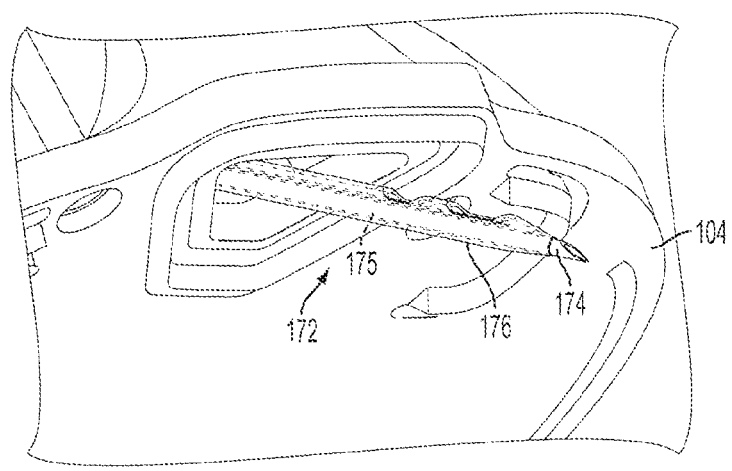
FIG. 4 is a bottom perspective view of the needle and cannula extending from the fluid delivery device in the intermediate position shown in FIG. 3.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory infusion device.

In other embodiments, a fluid delivery device may be used to deliver a therapeutic fluid to a patient with integrated monitoring. In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid deliver device 100. The fluid delivery device 100 may also include a housing 104 to enclose the circuit board 101, the chassis 102, and the components 110, 130, 150, 170, 180.

The fluid delivery device 100 may also include integrated monitoring. A monitor test strip 120 coupled to a monitor (not shown) in the device 100 may be introduced by the transcutaneous access tool 172 subcutaneously. The fluid delivery device 100 may be configured to receive data from the monitoring test strip concerning one or more physiologic conditions of the patient. For example, the fluid delivery device 100 may be configured to receive data from the monitoring test strip concerning a glucose level of the patient, and determining an output of a fluid such as insulin from the reservoir based on the glucose level. One example of the monitor test strip is a CGM test strip (such as the type available from Nova Biomedical) which may be understood as a glucose sensor configured to test for a concentration level of glucose in the blood of a patient.

The transcutaneous access tool 172 includes an introducer trocar or needle 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172. The transcutaneous access tool 172 may also be used to introduce a monitoring test strip subcutaneously into the patient for monitoring purposes, as described in greater detail below.

Figure 5:
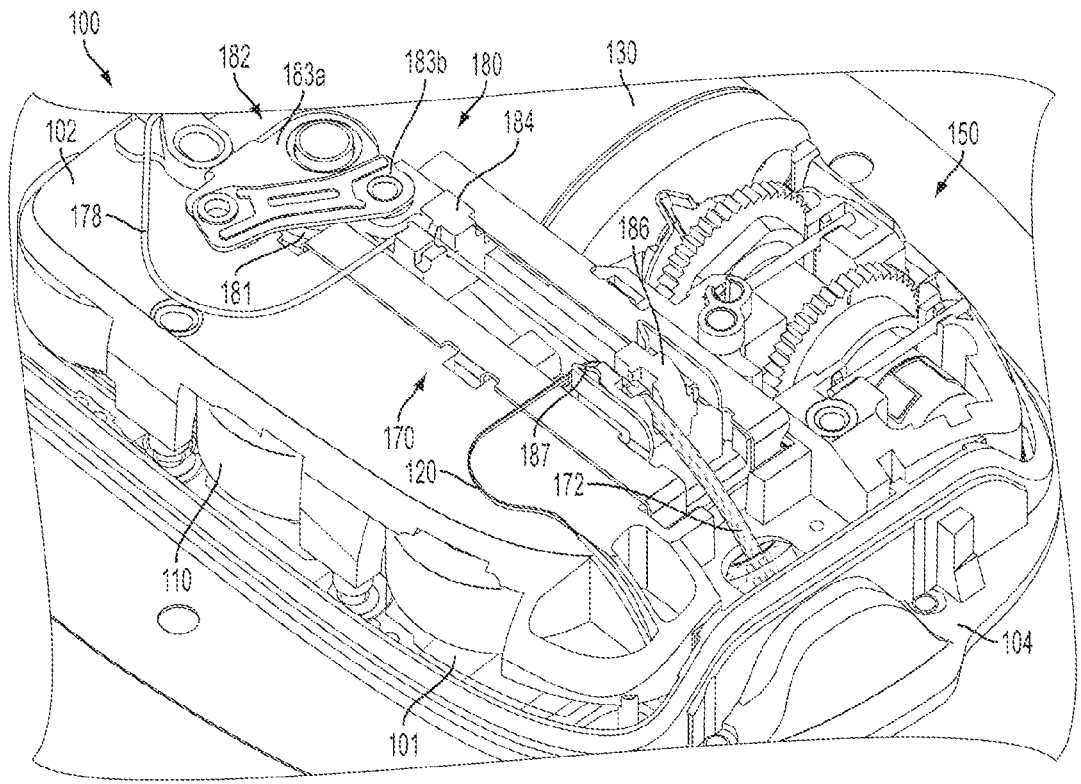
FIG. 5 is a top perspective view of the fluid delivery device shown in FIG. 1 with the insertion mechanism in a post-deployment position.
Figure 6:
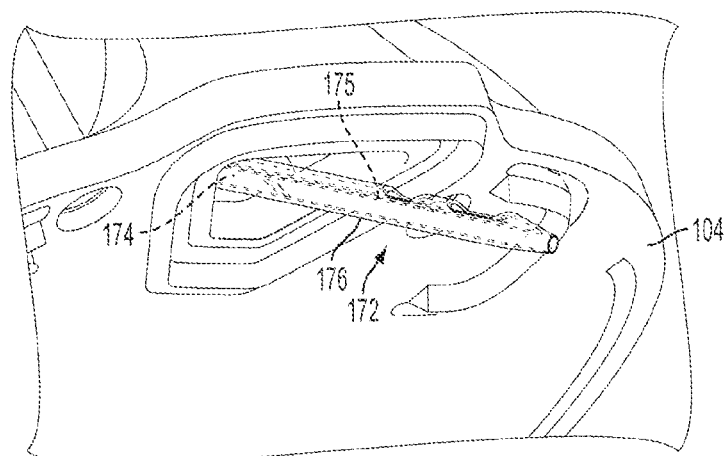
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

One embodiment of the spring-biased linkage mechanism 182 includes a helical torsion spring 181 and first and second linkages 183a, 183b coupled between the torsion spring 181 and the first sliding member 184. Energy stored in the torsion spring 181 applies a force to the linkages 183a, 183b, which applies a force to the first sliding member 184 to move the first sliding member 184 in both the insertion direction and in the retraction direction. In the pre-deployment position (FIG. 1), the torsion spring 181 is loaded and the sliding members 184, 186 are locked and prevented from moving. When the sliding members 184, 186 are released, the energy stored in the torsion spring 181 causes the first linkage 183a to rotate (e.g., clockwise as shown), which applies a force to the first sliding member 184 through the second linkage 183b causing the first sliding member 184 with the needle/trocar 174 to move (with the second sliding member 186) in the insertion direction. In the intermediate position (FIG. 3), the linkages 183a, 183b are fully extended with the needle/trocar 174 and cannula 176 being inserted, the second sliding member 186 is locked, and the remaining energy stored in the torsion spring 181 causes the first linkage 183a to continue to rotate, which applies an opposite force to the first sliding member 184 through the second linkage 183b causing the first sliding member 184 with the needle/trocar 174 to move in the retraction direction to the post-deployment position (FIG. 5). In the illustrated embodiment, the second sliding member 186 is locked against retraction by one or more latches 187. Thus, in the foregoing manner, the continuous uninterrupted clockwise rotation of first linkage 183a via the energy of torsion spring 181 provides the transcutaneous access tool insertion mechanism 180 with the ability to insert and retract the needle/trocar 174 in a single, uninterrupted motion.

The spring-biased linkage mechanism 182 allows a single spring and motion to achieve both the insertion and retraction and has a relatively small size. The spring-biased linkage mechanism 182 also reduces the static stresses caused by locking and holding back the sliding members 184, 186 and provides a smoother and more comfortable needle/trocar insertion because of the way the linkages 183a, 183b vector the forces applied to the sliding members 184, 186. The static forces on the sliding members 184, 186 are relatively small in the pre-deployment position when the linkages 183a, 183b are fully retracted. When the deployment starts and the linkages 183a, 183b start to become extended, the insertion forces increase because the force vectors increase in the insertion direction as the linkages extend 183a, 183b until a maximum insertion force is reached at the fully extended, intermediate position. By gradually increasing the insertion forces, the needle/trocar insertion and retraction is smoother, quieter and less painful.

Figure 7:
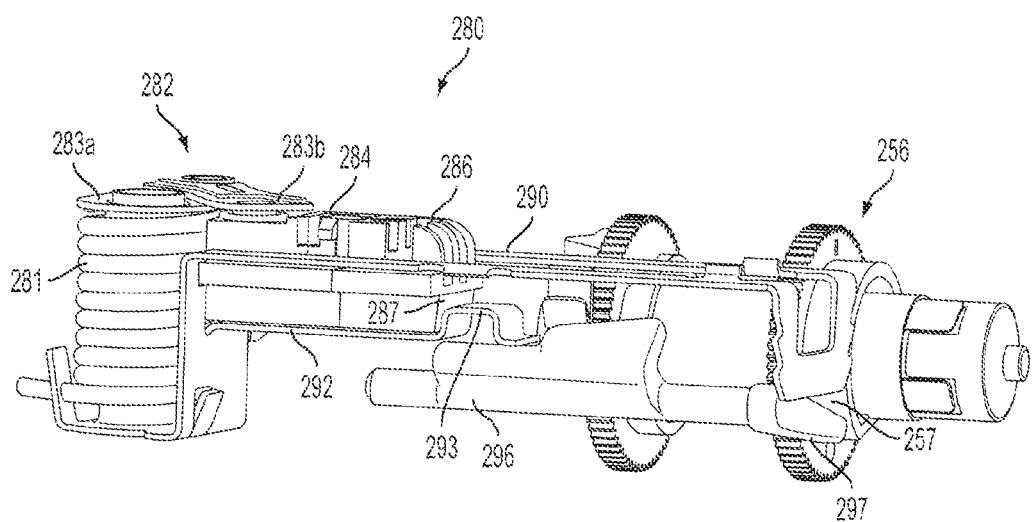
FIG. 7 is a side perspective view of another embodiment of the insertion mechanism, consistent with the present disclosure, in a pre-deployment position.
Figure 8:
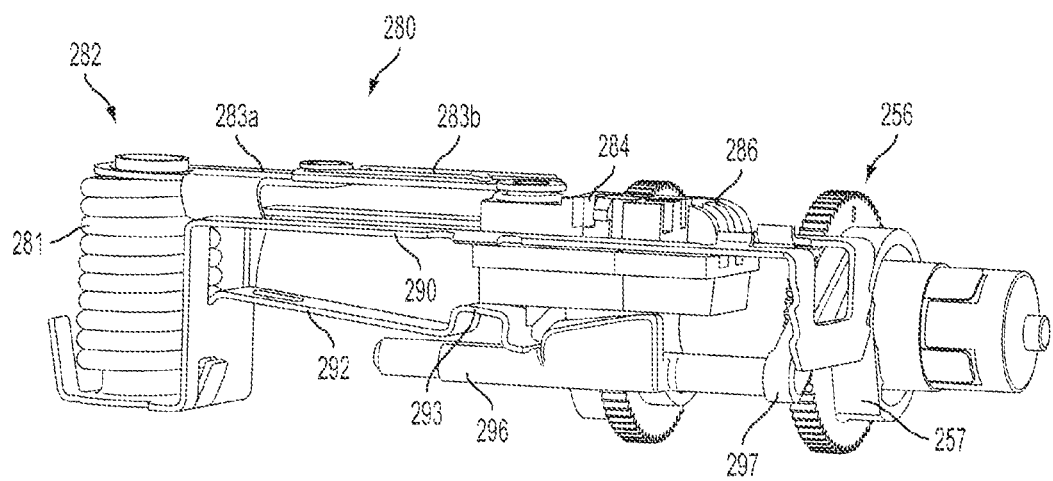
FIG. 8 is a side perspective view of the insertion mechanism shown in FIG. 7 in an intermediate position.

Another embodiment of an insertion mechanism 280 is shown in greater detail in FIGS. 7-10. The sliding members 284, 286 are slidably received in a frame 290 and moved by a spring-biased linkage mechanism 282 including torsion spring 281 and linkages 283a, 283b. In this embodiment, a cam finger 292 (e.g., extending from the frame 290) engages beneath one or both of the sliding members 284, 286 to lock the sliding members in the retracted or pre-deployment position (FIG. 7). In this pre-deployment position, the cam finger 292 is held against the sliding members 284, 286 by a release bar 296, which may be moved (rotated) to allow the cam finger 292 to move and release the sliding members 284, 286 (FIG. 8). The cam finger 292 may be biased in a downward direction and/or the second sliding member 286 may include a cam surface 287 to help facilitate movement along the cam finger 292 over locking mechanism 293 upon actuation.

The release bar 296 includes a lever 297 for pivoting the release bar 296 between an engaged position against the cam finger 292 (FIG. 7) and a disengaged position releasing the cam finger 292 (FIG. 8). The release bar 296 may be biased toward the disengaged position and held against the cam finger 292 in the engaged position until the lever 297 is released allowing the release bar 296 to move to the disengaged position. In the illustrated embodiment, the lever 297 engages a rotating surface 257 of a drive wheel 256 of the fluid drive mechanism 150 such that the lever 297 is held in the engaged position for part of the rotation and is released at a certain point during the rotation (e.g., when a flat portion of the rotating surface 257 allows the lever 297 to move).

Figure 9:
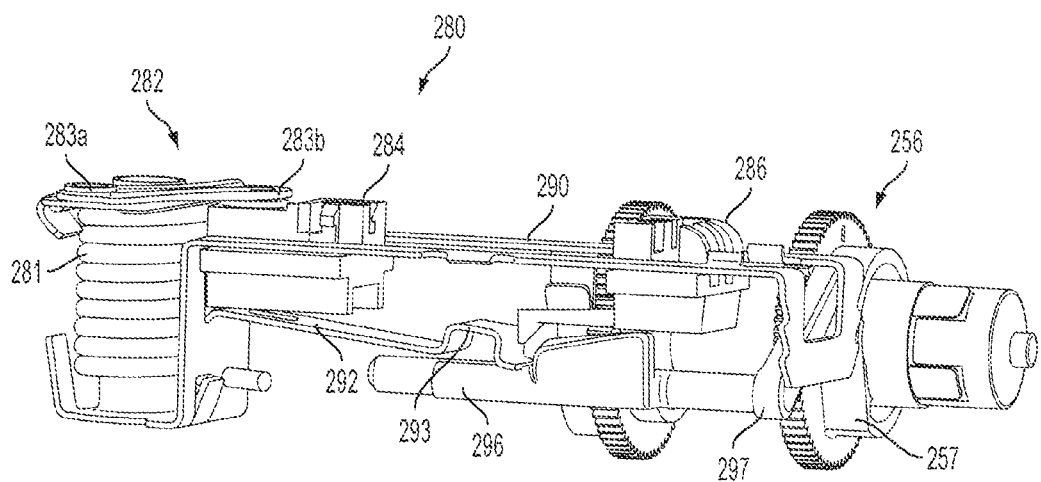
FIG. 9 is a side perspective view of the insertion mechanism shown in FIG. 7 in a post-deployment position.
Figure 10:
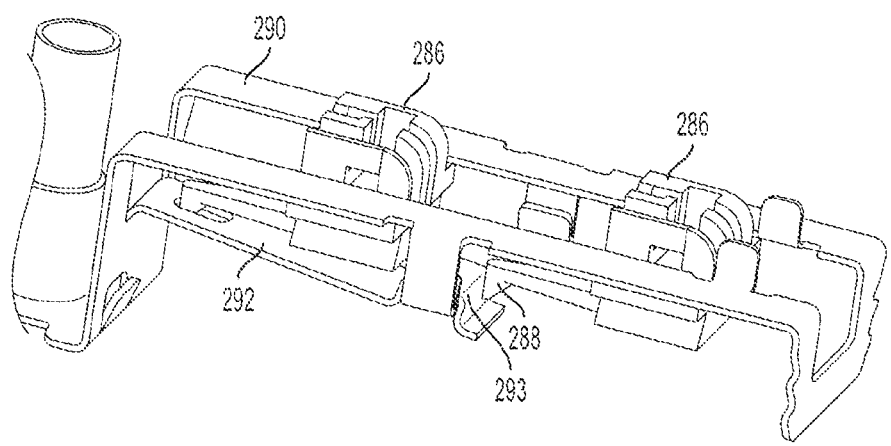
FIG. 10 is a top perspective view of the second sliding member of the insertion mechanism shown in FIG. 7 locked in the pre-deployment and post-deployment positions.

As shown in FIGS. 9 and 10, the cam finger 292 may also be used to lock the second sliding member 286 in the insertion position. A locking portion 288 of the second sliding member 286 engages a locking portion 293 of the cam finger 292 when the linkage mechanism 282 is fully extended in the intermediate position and prevents the second sliding member 286 from retracting such that the cannula remains inserted. As discussed above, the second sliding member 286 may also be locked by one or more latches (not shown) extending from a top of the frame 290.

Referring to FIGS. 11-16, one embodiment of the fluid drive mechanism 150 uses a clutch mechanism 160 to facilitate filling of the reservoir 130 and engagement of the fluid drive mechanism 150 for driving fluid out of the reservoir 130. The fluid drive mechanism 150 includes a first threaded member in the form of an elongated shaft such as a threaded drive rod or leadscrew 152, with external threads extending from a plunger 136 received in the reservoir 130 and sealed with an o-ring 137 against the inside surface of the reservoir 130. The leadscrew 152 and plunger 136 may be an inseparable, insert-molded assembly. A second threaded member in the form of an elongated shaft such as a tube nut 154 with internal threads threadably engages the leadscrew 152 and may be driven by a drive wheel 156 via a clutch mechanism 160.

When the reservoir 130 is empty (FIGS. 11 and 12), the plunger 136 is positioned at one end of the reservoir 130 such that the plunger 136 is extended and the clutch mechanism 160 is disengaged. In certain embodiments, the reservoir 130 may be filled with fluid by opening an inlet port to the reservoir 130 and pumping in the fluid under sufficient hydraulic pressure to retract the plunger 136 within the reservoir 130. Thereafter, the inlet port may be closed. When the reservoir 130 is filled and the plunger 136 moves to the opposite (retracted) end of the reservoir 130 (FIG. 13), the clutch mechanism 160 remains disengaged to allow the tube nut 154 to pass into an elongated cylindrical bore (along the drive axis) of a hub of the drive wheel 156. The clutch mechanism 160 may then be engaged (FIGS. 14-16) such that rotation of the drive wheel 156 causes the clutch mechanism 160 to rotate the tube nut 154, which causes the leadscrew 152 to advance the plunger into the reservoir 130 to deliver the fluid from the reservoir 130. In alternative embodiments, the reservoir 130 may be filled when the plunger 136 is already retracted.

Figure 11:
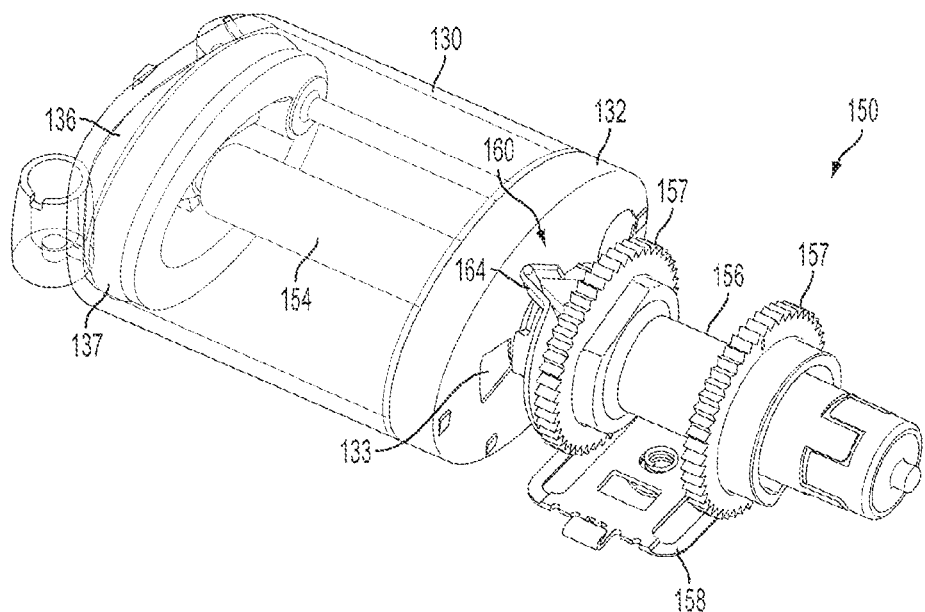
FIG. 11 is a top perspective view of a fluid driving mechanism of the fluid delivery device shown in FIG. 1 with a clutch mechanism in a disengaged position prior to filling.
Figure 12:
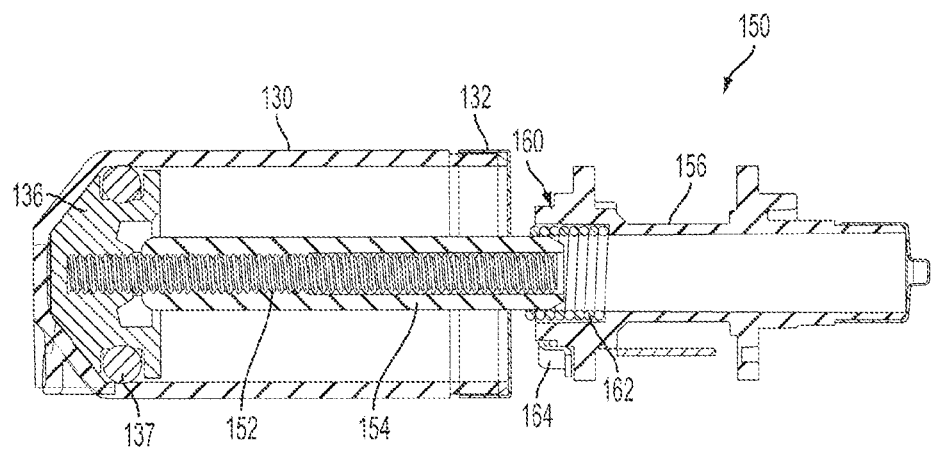
FIG. 12 is a side cross-sectional view of the fluid driving mechanism shown in FIG. 11.
Figure 13:
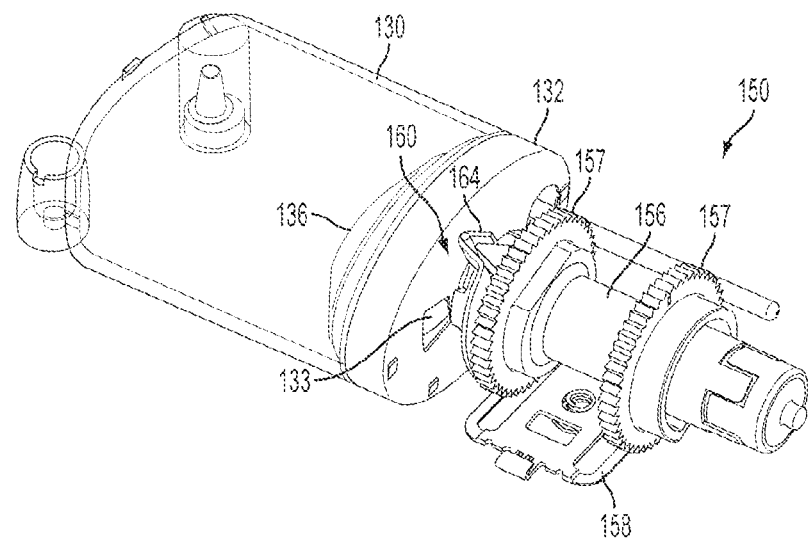
FIG. 13 is a top perspective view of the fluid driving mechanism shown in FIG. 11 with the clutch mechanism in a disengaged position after filling.
Figure 14:
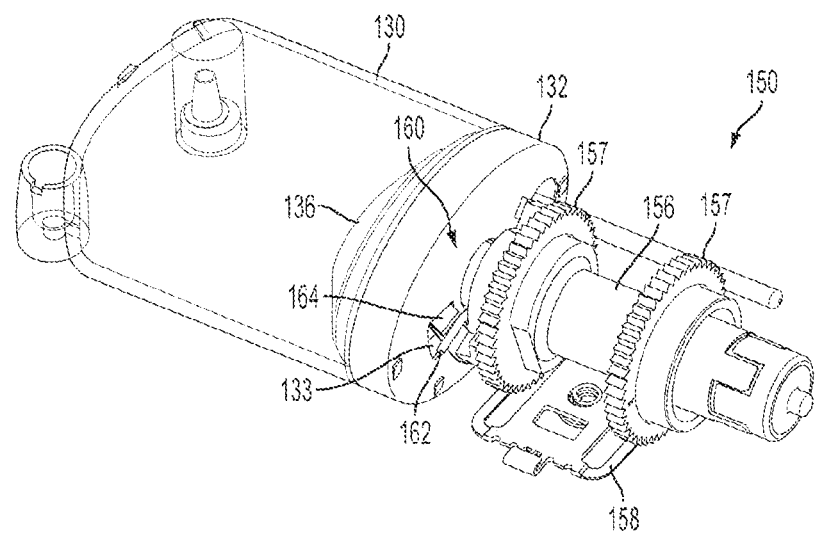
FIG. 14 is a top perspective view of the fluid driving mechanism shown in FIG. 11 with the clutch mechanism being released to the engaged position.
Figure 15:
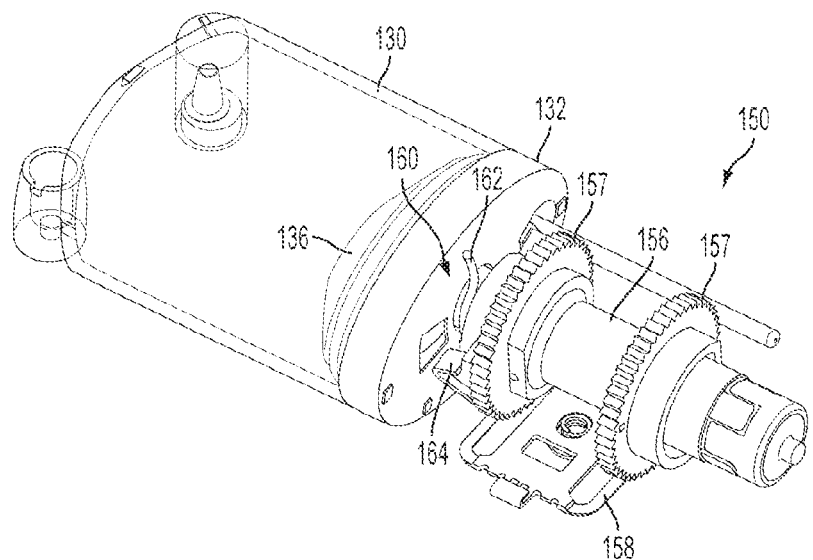
FIGS. 15 and 16 are top perspective views of the fluid driving mechanism shown in FIG. 11 with the clutch mechanism in the engaged position.
Figure 16:
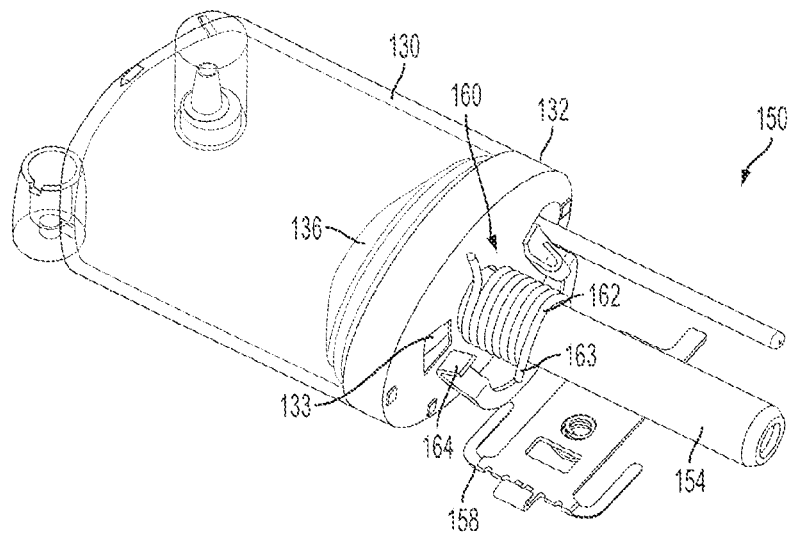
Figure 17:
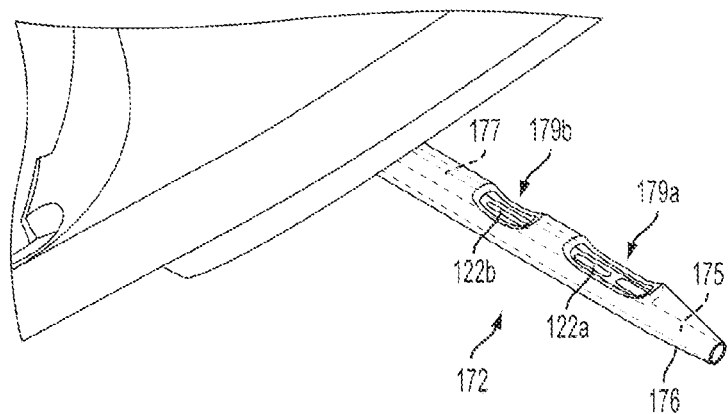
FIGS. 17-23 are views of a bi-lumen cannula used in the fluid delivery device shown in FIGS. 1-6 to insert a monitor test strip transcutaneously.
Figure 18:
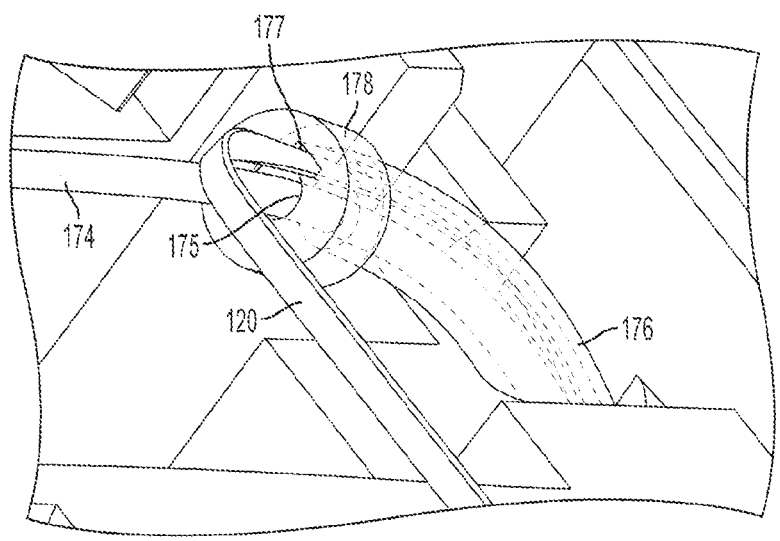
Figure 19:
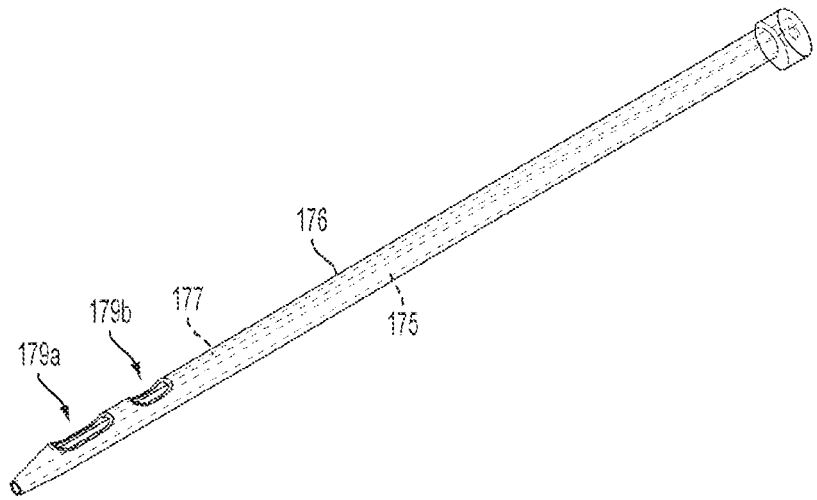
Figure 20:
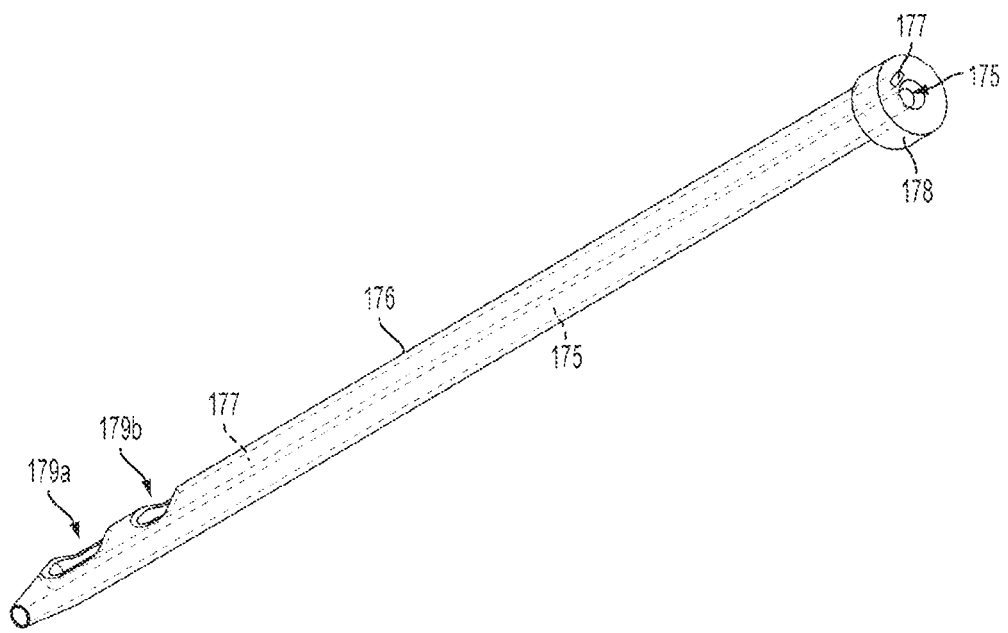
Figure 21:
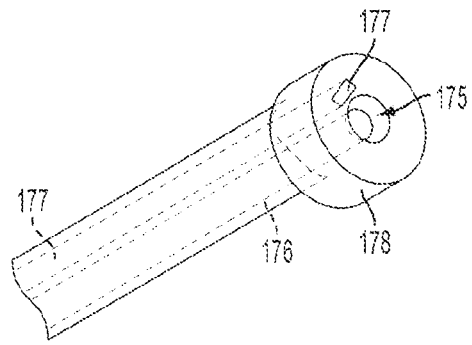
Figure 22:
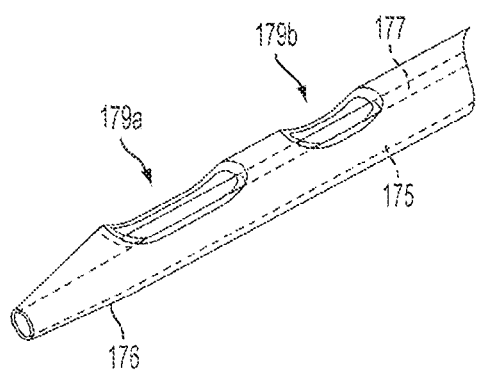
Figure 23:
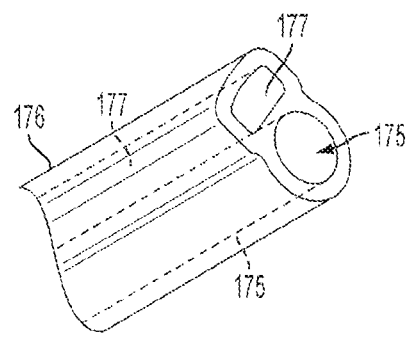
Figure 24:
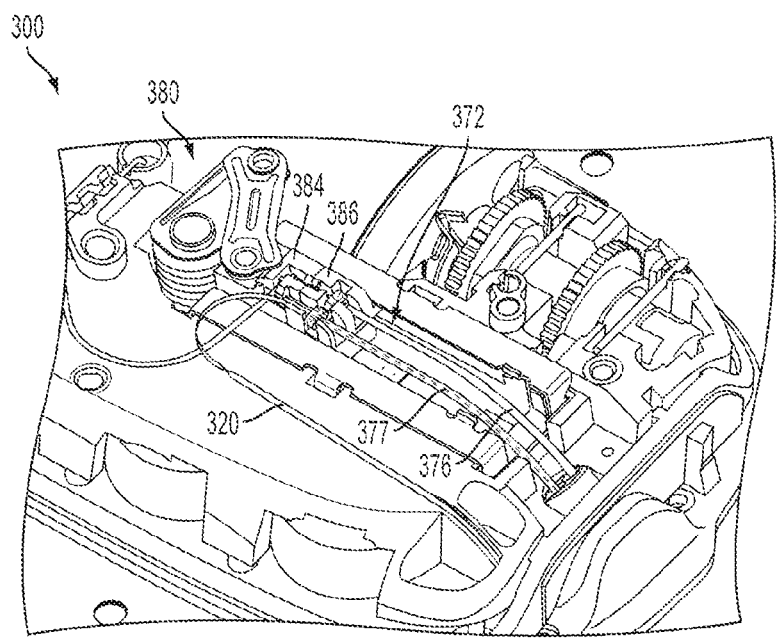
FIGS. 24-29 are views of another embodiment of a fluid delivery device including a cannula with a D-shaped lumen for inserting a monitor test strip transcutaneously.
Figure 25:
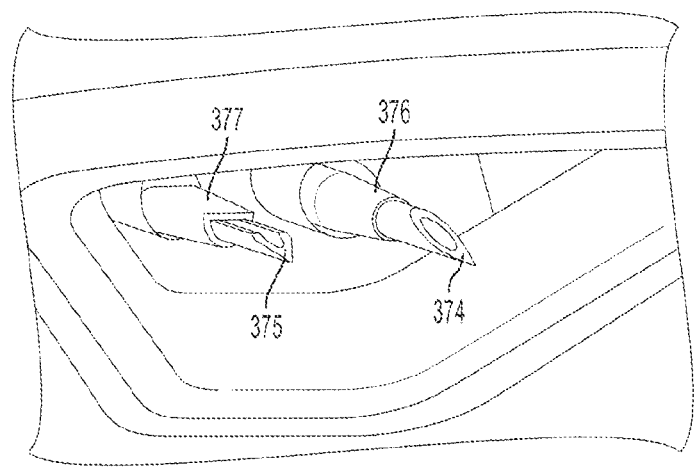
Figure 26:
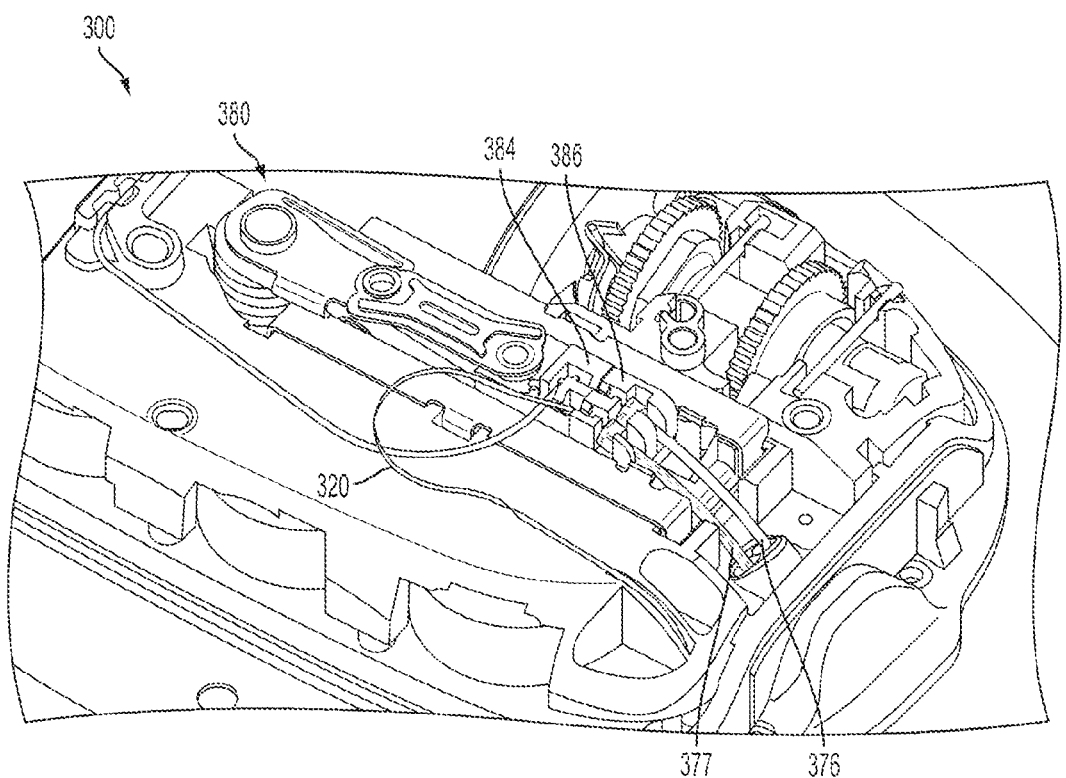
Figure 27:
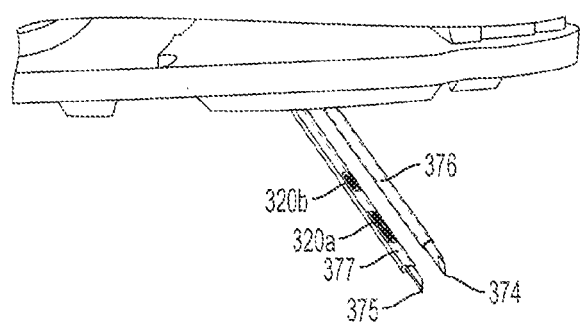
Figure 28:
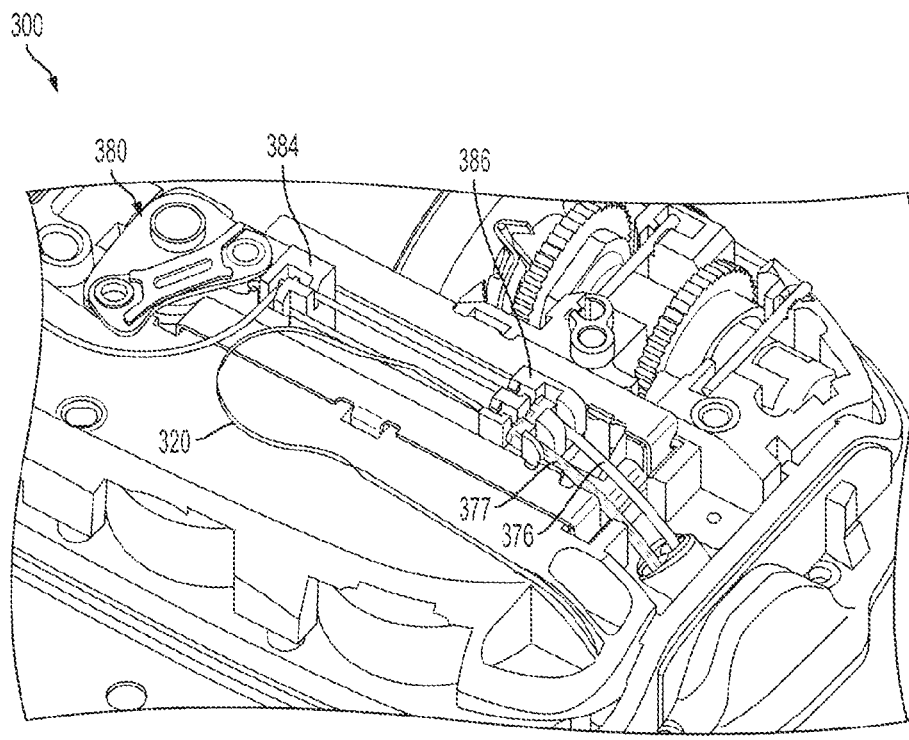
Figure 29:
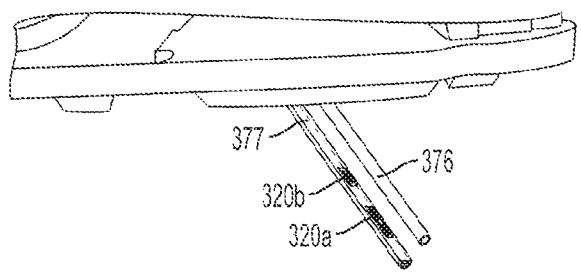
Figure 30:
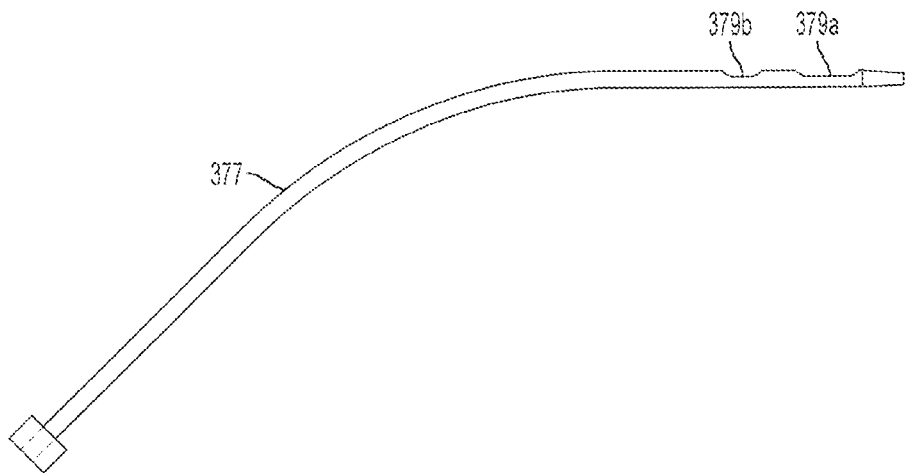
FIGS. 30-32 are views of the D-lumen cannula used in the fluid delivery device of FIGS. 24-29.
Figure 31:
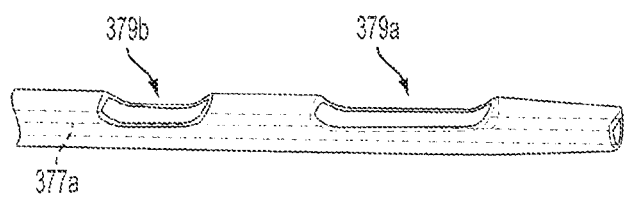
Figure 32:
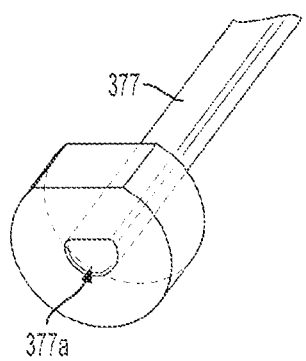
Figure 33:
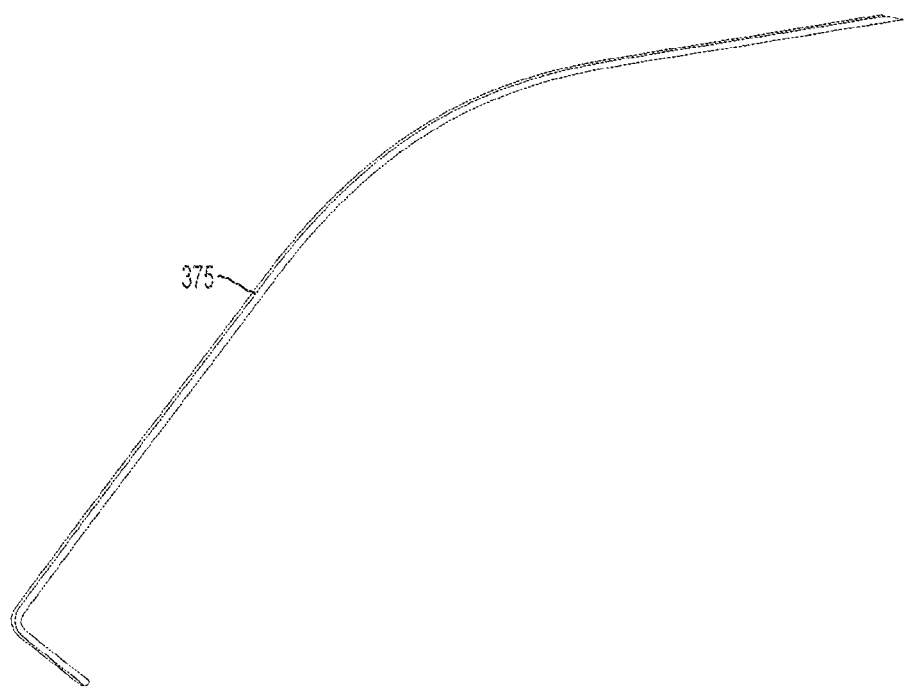
FIGS. 33 and 34 are views of a semi-circular trocar used with the D-lumen cannula in the fluid delivery device of FIGS. 18-23.
Figure 34:
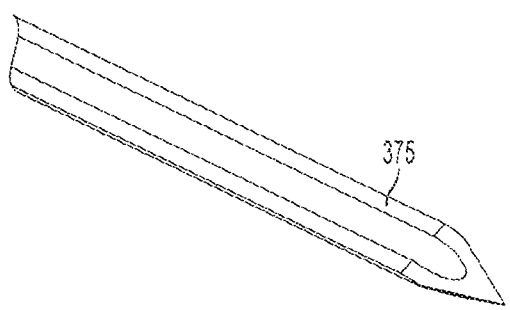
Figure 35:
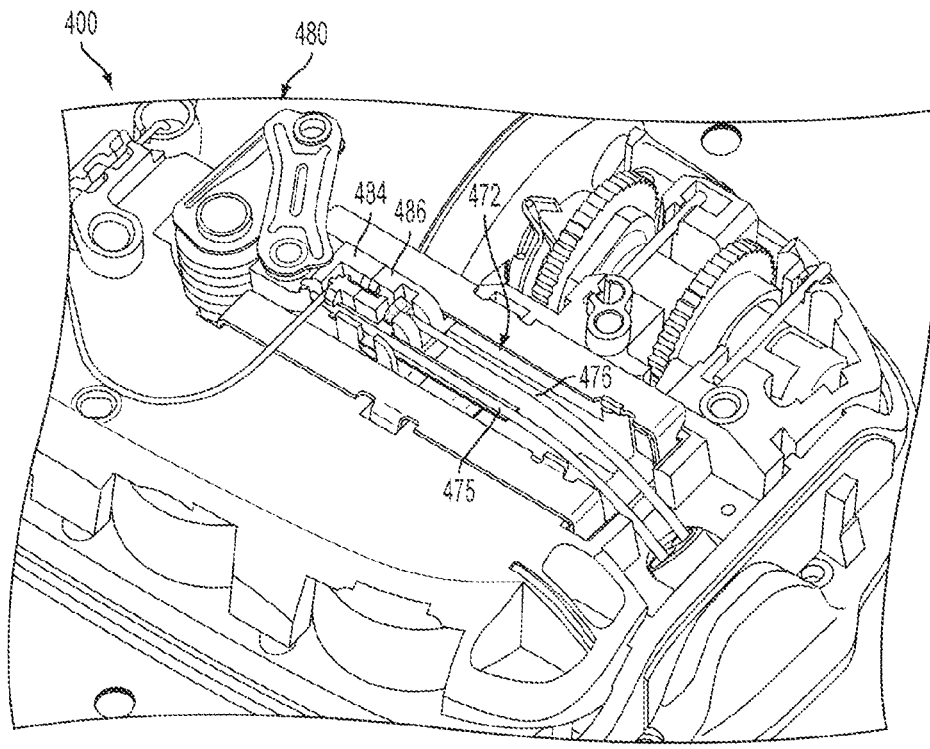
Figure 36:
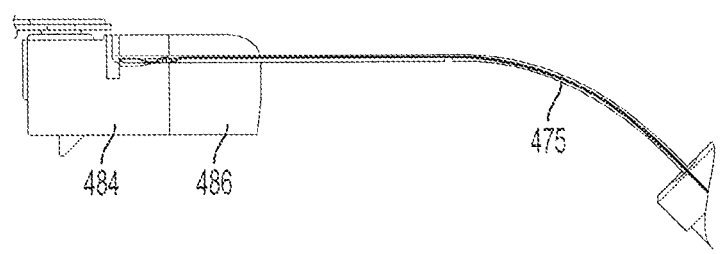
Figure 37:
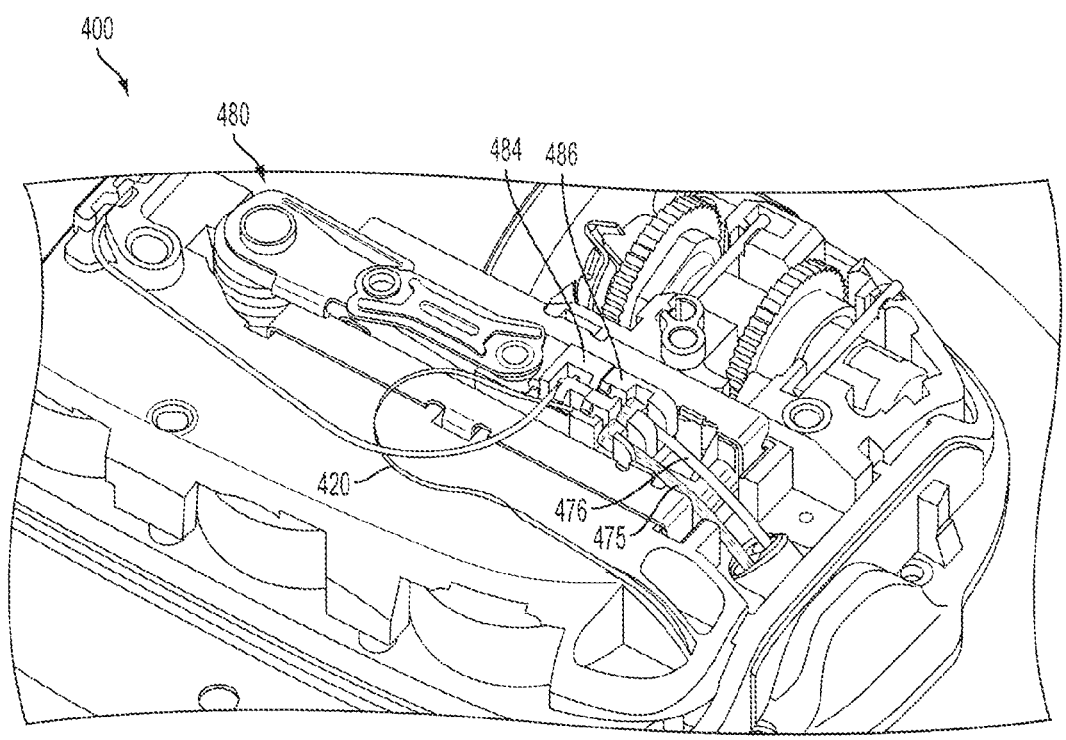
Figure 38:
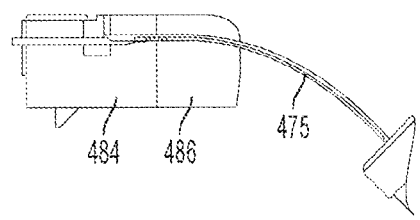

In the illustrated embodiment, the clutch mechanism 160 includes a clutch spring 162 (e.g., a helical torsion spring) located in a counterbore at one end of the drive wheel 156, adjacent the reservoir 130. The inside diameter of the clutch spring 162 is larger than the outside diameter of the tube nut 154 when the clutch spring 162 is loaded, thereby disengaging the clutch spring 162 from the tube nut 154 and allowing the tube nut 154 to pass through the center aperture of the spring 162 and into the elongated bore of the drive wheel 156. Alternatively, the inside diameter of the clutch spring 162 is smaller than the outside diameter of the tube nut 154 when the clutch spring 162 is unloaded, thereby engaging or gripping the tube nut 154 and allowing the drive wheel 156 to rotate the tube nut 154. In the illustrated embodiment, prior to filing the reservoir 130, the clutch spring 162 is held in the loaded, disengaged position by a spring latch 164 engaged with the drive wheel 156 (FIGS. 11-13). After the reservoir 130 has been filled, the clutch spring 162 may thus be engaged by rotating the drive wheel 156 until the spring latch 164 releases the clutch spring 162 (FIG. 14) allowing the clutch spring 162 to unload and grip the tube nut 154 (FIGS. 15 and 16), at which time fluid may be dispensed from the reservoir 130 with continued rotation of the drive wheel 156.

As shown, the spring latch 164 may be biased by the clutch spring 162 such that as the drive wheel 156 rotates the spring latch 164 moves rotationally against a surface of a reservoir cap 132 until clutch spring 162 deflects the spring latch 164 into a window 133 in the reservoir cap 132. When the spring latch 164 moves into the window 133, the end of the clutch spring 162 held by the spring latch 164 is released, thus engaging the clutch mechanism 160. When the clutch spring 162 is engaged, the drive wheel 156 contacts an end 163 of the clutch spring 162 to create a thrust on the clutch spring 162 that causes the clutch spring 162 to rotate the tube nut 154. The fluid drive mechanism 150 may also use other clutch mechanisms capable of allowing the tube nut 154 or other type of nut or threaded member to pass through the clutch mechanism and then being activated to engage the nut or threaded member.

In the illustrated embodiment, the drive wheel 156 includes ratchets 157 that are engaged by an actuator 158 to incrementally drive the wheel 156 and advance the plunger 136 into the reservoir 130. Examples of this actuation mechanism are described in greater detail in U.S. Patent Application Publication No. 2005/0238507, which is fully incorporated herein by reference.

By using a clutch mechanism, the engagement between the leadscrew and the nut occurs at assembly, and thus no rotation is needed for the nut to engage the leadscrew by operation of the device. This reduces the number of fluid path prime pulses to prime the pump and assures a full and proper priming of the fluid path before placement on the body. The clutch mechanism also enables the changing of thread pitch for other drug applications without a need to redesign the tilt nut used in fluid driving mechanisms in other existing pumps. The components of the clutch mechanism are also more easily inspected than the tilt nut assembly.

According to one embodiment, as shown in FIGS. 17-23, the cannula 176 providing the transcutaneous access for delivery the fluid may also be used to introduce the monitor test strip 120. In this embodiment, the cannula 176 includes a first lumen 175 for receiving the needle/trocar 174 and a second lumen 177 for receiving the test strip 120. As shown, the first lumen 175 has a circular (cylindrical) profile and the second lumen 177 has a rectangular profile. The cannula 176 may also include one or more windows 179a, 179b providing access to one or more sensors 122a, 122b on the test strip 120. As shown, the plurality of windows 179a, 179b of the cannula 176 may be arranged on a same side of the sidewall of cannula 176, with the first window 179a arranged at a distance from the distal end tip of the cannula 176 which is less than the distance of the second window 179b from the distal end tip of the cannula 176.

To insert the test strip 120 into second lumen 177, the test strip 120 passes into second lumen 177 at the head 178 of the cannula 176 and extends to the window(s) 179a, 179b. Thus, at least one window 179a, 179b exposes a sensor 122a, 122b of the monitoring test strip 120. In the example embodiment, two windows 179a, 179b are provided with the window 179a closest to the tip of the cannula 176 providing access to the main sensor area and the window 179b farthest from the tip providing a reference. Although a specific shape and configuration of a bi-lumen cannula is shown, other configurations of a cannula with first and second lumens may also be used to both deliver a therapeutic fluid and introduce a test strip subcutaneously.

According to another embodiment, as shown in FIGS. 24-34, a fluid delivery device 300 may include a transcutaneous access tool 372 with a first cannula 376 for delivering fluid and a second cannula 377 for introducing a test strip 320. The first cannula 376 receives a first needle/trocar 374 (shown as a circular needle) to facilitate insertion of the first cannula 376 and the second cannula 377 receives a second needle/trocar 375 (shown as a semi-circular trocar) to facilitate insertion of the second cannula 377. The fluid deliver device 300 includes an insertion mechanism 380, similar to the first described embodiment above, but with sliding members 384, 386 coupled to both the needle 374 and the trocar 375 and both cannulas 376, 377. The insertion mechanism 380 inserts the second cannula 377 and the trocar 375 and then retracts the trocar 375 in the same manner as described above. The test strip 320 remains inserted after the trocar 375 is retracted. Thus, both the first needle/trocar 374 and the second needle/trocar 375 may be introduced into the patient simultaneously, particularly to reduce the pain of sequential insertions.

Similar to the above described embodiment, first cannula 376 includes a circular (cylindrical) lumen 376a. As shown in greater detail in FIGS. 30-32, the second cannula 377 includes a semi-circular (D-shaped) lumen 377a to allow the monitor strip to sit relatively flat within the cannula 377. The second cannula 377 also includes one or more windows 379a, 379b providing access to one or more sensors 320a, 320b on the test strip 320 (see FIGS. 27 and 29). As shown, similar to the prior embodiment, the plurality of windows 379a, 379b, of the cannula 377 may be arranged on a same side of the sidewall of the cannula 377, with the first window 379a arranged at a distance from the distal end tip of the cannula 377 which is less than the distance of the second window 379b from the distal end tip of the cannula 377. Thus, at least one window 379a, 379b exposes a sensor 320a, 320b of the monitoring test strip 320. In the example embodiment, two windows 379a, 379b are provided with the window 379a closest to the tip of the cannula 377 providing access to the main sensor area and the window 379b farthest from the tip providing a reference. As shown in greater detail in FIGS. 33 and 34, the trocar 375 has a shape corresponding to the D-shaped lumen 377a to allow the trocar 375 to be retracted leaving the test strip 320 inserted (see FIG. 29). As shown, the trocar includes a planar side surface 373 which corresponds to a planar test strip 320 such that, when assembled, the planar test strip 320 may be located adjacent the planar side surface 373 of the trocar 375 in the second cannula 377.

According to another embodiment, as shown in FIGS. 35-43, a fluid delivery device 400 may include a transcutaneous access tool 472 with a cannula 476 for delivering fluid and a needle or trocar 475 (shown as a semi-circular trocar) for introducing a test strip 420. The cannula 476 receives a needle/trocar 474 (shown as circular needle) to facilitate insertion of the cannula 476 and the trocar 475 is inserted with the test strip 420. The fluid deliver device 400 includes an insertion mechanism 480, similar to the first described embodiment above, but with sliding members 484, 486 coupled to both the needle 474 and the trocar 475. The insertion mechanism 480 inserts the trocar 475 (FIGS. 37 and 38) and then retracts the trocar 475 (FIGS. 39 and 40) in the same manner as the needle/trocar described above. The test strip 420 remains inserted after the trocar 475 is retracted (FIG. 41). In contrast to the prior embodiment, the needle/trocar 475 introduces the monitoring test strip 420 subcutaneously solely (i.e. without the monitoring test strip 420 being introduced with a cannula).

Figure 42:
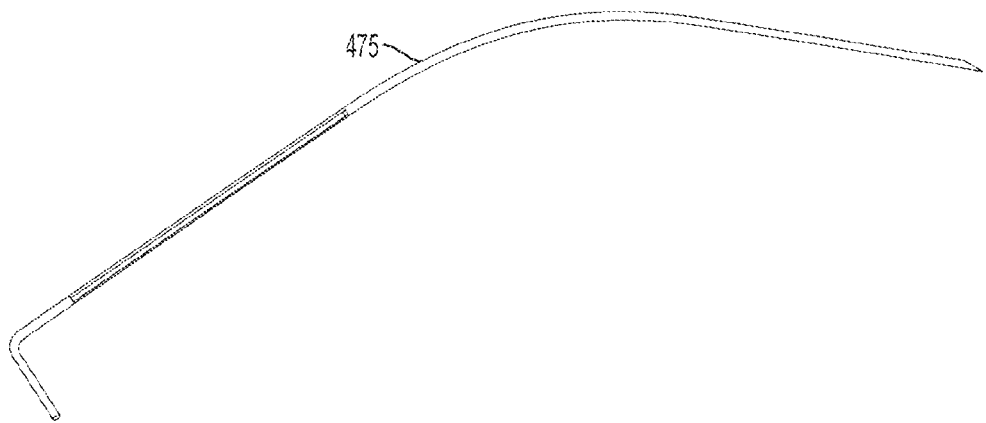
FIG. 42 is a side view of the oval trocar for use in the fluid delivery device shown in FIGS. 35-41.
Figure 43:
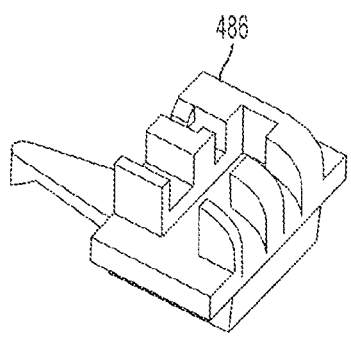
FIG. 43 is a top perspective view of a second sliding member for use in the fluid delivery device shown in FIGS. 35-41.

The trocar 475 is shown in greater detail in FIG. 42. The second sliding member 486 is shown in greater detail in FIG. 43. In this embodiment, the second sliding member 486 is designed to capture the cannula 476 and to receive and allow the trocar 475 to pass through.

Accordingly, various embodiments of the fluid delivery device may use the transcutaneous access tool both to deliver fluid and to introduce a test strip subcutaneously to provide integrated monitoring.

In certain embodiments, an operational sequence of fluid delivery device 100 (or 300 or 400) of the present disclosure may be automatically triggered or otherwise initiated based upon a filling of the fluid reservoir 130 with a fluid to a predetermined fill level. For example, the fluid reservoir 130 may include a fluid fill sensor which provides feedback of the fluid fill level, which may be an input to a computer instruction program stored in non-transitory memory and run by a computer processor stored and located with the circuit board 101 of the fluid delivery device 100.

Prior to the fluid reservoir 130 being filled with fluid, the fluid delivery device 100, and more particularly the computer processor, may be in a stand-by (e.g. sleep) mode. Once the computer processor detects an input signal from the fluid fill sensor that the fluid in the fluid reservoir 130 has reached the predetermined fill level, the computer processor may execute a computer program which includes instructions to automatically operate the transcutaneous access tool insertion mechanism 180 within a transcutaneous access tool introduction time period, which may also be understood as a predetermined deployment time period, i.e. the time period between the filling of the fluid reservoir 130 and the insertion of the needle/trocar 174 and cannula 176 through the skin of a patient.

For example, a clinician may fill the fluid reservoir 130 with a therapeutic fluid at a clinic, which results in the fluid fill sensor sending an input signal which is detected by the computer processor as to the filled status of the fluid reservoir 130. Upon receiving the input signal from the fluid fill sensor, the operational computer program for the fluid delivery device 100 being run by the computer processor may instruct the fluid delivery device 100 to operate the transcutaneous access tool insertion mechanism 180 within the transcutaneous access tool introduction time period. During the transcutaneous access tool introduction time period, the clinician may properly position and locate the fluid delivery device 100 on the patient. The transcutaneous access tool introduction time period should be long enough to properly install the fluid delivery device 100 on the patient, but not so long that the clinician and patient have to wait a substantial time for the transcutaneous access tool insertion mechanism 180 to operate.

In certain embodiments, the transcutaneous access tool introduction time period may be greater than or equal to 30 seconds, and less than or equal to 15 minutes. More particularly, the transcutaneous access tool introduction time period may be greater than or equal to 1 minute, and less than or equal to 10 minutes. Even more particularly, the transcutaneous access tool introduction time period may be greater than or equal to 2 minutes, and less than or equal to 5 minutes.

It may also be desirable to delay the onset of infusion for an infusion delay time period after insertion of the needle/trocar 174 and cannula 176 through the skin of a patient. For example, it may be desirable to delay infusion of the fluid from fluid reservoir 130 if such may adversely react with, or be rendered less effective by, a first composition already in the patient, such as another therapeutic composition, which may also be a therapeutic fluid.

In such instance, it may be desirable to automatically delay infusion of the fluid from fluid reservoir 130 until the first therapeutic composition in the patient decreases to levels of less than 20% (and more particularly less than 10%, and even more particularly less than 5%) of a concentration level in the patient as compared to the concentration level when the first therapeutic composition is introduced to the patient.

Given that it may not be possible to accurately predict the rate of decrease in concentration of a therapeutic composition in the patient, it may be desirable to delay infusion of the fluid from fluid reservoir 130 for a predetermined infusion delay time period.

For example, the infusion delay time period between the insertion of the needle/trocar 174 and cannula 176 through the skin of a patient and the infusion of the fluid from the fluid reservoir may be at least 1 hour. In other embodiments, the infusion delay time period may be at least 2 hours, at least 4 hours, at least 8 hours, at least 12 hours, at least 16 hours, at least 20 hours, at least 24 hours, at least 28 hours, at least 32 hours, at least 36 hours, at least 40 hours, at least 44 hours, at least 48 hours, at least 52 hours, at least 56 hours, at least 60 hours, at least 64 hours, at least 68 hours or at least 72 hours.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A medical device comprising: an infusion device comprising a fluid reservoir to contain a therapeutic fluid and a transcutaneous access tool fluidly coupled to the fluid reservoir, the transcutaneous access tool configured to deliver the therapeutic fluid subcutaneously to a patient; wherein the infusion device operates in a stand-by mode prior to the therapeutic fluid being introduced into the fluid reservoir, and wherein, upon filling the fluid reservoir to a predetermined fill level with the therapeutic fluid when the infusion device is in stand-by mode, the infusion device generates a signal indicative that the fluid reservoir has been filled to the predetermined fill level with the therapeutic fluid, wherein, upon generating the signal indicative that the fluid reservoir has been filled to the predetermined fill level with the therapeutic fluid, the infusion device uses the signal to cause automatic deployment of the transcutaneous tool once at least one processer detects the signal from at least one sensor that the fluid in the fluid reservoir has reached the predetermined fill level, and wherein the automatic deployment of the transcutaneous tool occurs during a predetermined deployment time period, the predetermined deployment time period initiated by the occurrence of the filling of the fluid reservoir.

2. The medical device of claim 1 wherein: the predetermined deployment time period is greater than or equal to 30 seconds.

3. The medical device of claim 1 wherein: the predetermined deployment time period is less than or equal to 15 minutes.

4. The medical device of claim 1 wherein: the predetermined deployment time period is greater than or equal to 1 minute, and less than or equal to 10 minutes.

5. The method of claim 1 wherein: the predetermined deployment time period is greater than or equal to 2 minutes, and less than or equal to 5 minutes.

6. The medical device of claim 1 wherein: the infusion device comprises non-transitory memory including stored instructions for the predetermined deployment time period, that when executed by the at least one processor, cause an instruction to be sent from the non-transitory memory to deploy the transcutaneous access tool within the predetermined deployment time period.

7. The medical device of claim 6 wherein: the at least one sensor operates by sending the signal to the at least one processor when the therapeutic fluid in the fluid reservoir reaches the predetermined fill level.

8. The medical device of claim 7 wherein:
the at least one processor operates by detecting the signal from the at least one sensor; and
upon detecting the signal from the at least one sensor, the at least one processor operates to execute the instructions that cause the infusion device to deploy the transcutaneous access tool.

9. The medical device of claim 1 wherein: the infusion device operates to deliver the therapeutic fluid in the fluid reservoir through the transcutaneous access tool after a predetermined infusion delay time period.

10. The medical device of claim 9 wherein: the infusion device operates to initiate the predetermined infusion delay time period when the transcutaneous access tool is deployed.

11. The medical device of claim 10 wherein: the predetermined infusion delay time period is at least 1 hour.

12. The medical device of claim 10, wherein: the predetermined infusion delay time period is at least 8 hours.

13. The medical device of claim 10 wherein: the predetermined infusion delay time period is at least 16 hours.

14. The medical device of claim 10 wherein: the predetermined infusion delay time period is at least 20 hours.

15. The medical device of claim 1 wherein: the transcutaneous access tool comprises a cannula.

16. The medical device of claim 1 wherein: the infusion device comprises an infusion pump.

* * * * *